US012783788B2

(12) United States Patent
Shapiro et al.

(10) Patent No.: US 12,783,788 B2
(45) Date of Patent: Nov. 3, 2026

(54) DYNAMIC IN-TRANSIT STRUCTURING OF UNSTRUCTURED MEDICAL DOCUMENTS

(71) Applicant: xCures, Inc., Oakland, CA (US)

(72) Inventors: Mark A. Shapiro, Durham, NC (US); Bryan J. Federowicz, Raleigh, NC (US); Glenn A. Kramer, San Francisco, CA (US)

(73) Assignee: XCURES, INC., Oakland, CA (US)

( * ) Notice: Subject to any disclaimer, the term of this patent is extended or adjusted under 35 U.S.C. 154(b) by 807 days.

(21) Appl. No.: 18/122,187

(22) Filed: Mar. 16, 2023

(65) Prior Publication Data

US 2023/0325582 A1 Oct. 12, 2023

Related U.S. Application Data

(63) Continuation of application No. PCT/US2021/050640, filed on Sep. 16, 2021.

(Continued)

(51) Int. Cl.

| | |
|---|---|
| ***G06F 40/151*** | (2020.01) |
| ***G06F 40/123*** | (2020.01) |
| ***G06F 40/205*** | (2020.01) |
| ***G06N 20/00*** | (2019.01) |
| ***G16H 10/60*** | (2018.01) |
| ***G16H 15/00*** | (2018.01) |

(52) U.S. Cl.

CPC .......... *G06F 40/151* (2020.01); *G06F 40/123* (2020.01); *G06F 40/205* (2020.01); *G06N 20/00* (2019.01); *G16H 10/60* (2018.01); *G16H 15/00* (2018.01)

(58) Field of Classification Search

CPC ..................................................... G06F 40/151
USPC ............................. 715/234; 726/27; 707/748
See application file for complete search history.

(56) References Cited

U.S. PATENT DOCUMENTS

2005/0120029 A1* 6/2005 Tomic ..................... G06F 16/86
2009/0287685 A1 11/2009 Charnock et al.

(Continued)

FOREIGN PATENT DOCUMENTS

JP 2015523379 A 8/2015
JP 2017513484 A 6/2017

(Continued)

OTHER PUBLICATIONS

Kurasawa, James H. et al.: Chemically Defined, High-Density Insect Cell-Based Expression System for Scalable AAV Vector Production. Molecular Therapy Methods & Clinical Development 19:330-340 (2020).

(Continued)

*Primary Examiner* — Mohammad Ali

(74) *Attorney, Agent, or Firm* — Wilson Sonsini Goodrich & Rosati

(57) ABSTRACT

Provided are systems and methods for dynamically transforming an unstructured document to a structured document prior to, during, or subsequent to transfer of information via the unstructured document. The transformation may be based on processing a variety of factors, such as the content of the unstructured document, request from a first party transferring the document, identity or characteristics of the first party, request from a second party requesting the document, and identity or characteristics of the second party.

50 Claims, 8 Drawing Sheets

Related U.S. Application Data

(60) Provisional application No. 63/080,591, filed on Sep. 18, 2020.

(56) References Cited

U.S. PATENT DOCUMENTS

| | | | | |
|---|---|---|---|---|
| 2010/0114899 | A1 | 5/2010 | Guha et al. | |
| 2012/0216290 | A1 * | 8/2012 | Roy | G06F 21/6227 726/27 |
| 2012/0284039 | A1 | 11/2012 | Kass-Hout et al. | |
| 2013/0124523 | A1 | 5/2013 | Rogers et al. | |
| 2015/0169676 | A1 * | 6/2015 | Bohra | G06F 40/258 707/748 |
| 2017/0154031 | A1 * | 6/2017 | Krishnamurthy | G06N 5/04 |
| 2019/0355483 | A1 | 11/2019 | Smurro | |
| 2020/0210490 | A1 * | 7/2020 | Hutchins | G06V 30/416 |
| 2021/0256156 | A1 * | 8/2021 | Enuka | G06F 21/6245 |

FOREIGN PATENT DOCUMENTS

| | | | | |
|---|---|---|---|---|
| WO | WO-02077855 | A1 * | 10/2002 | H04L 67/565 |
| WO | WO-2004042507 | A2 * | 5/2004 | G06F 16/9577 |
| WO | WO-2014045674 | A1 | 3/2014 | |
| WO | WO-2020061574 | A1 | 3/2020 | |
| WO | WO-2021142447 | A1 | 7/2021 | |

OTHER PUBLICATIONS

EP201870203.3 Extended European Search Report dated Sep. 9, 2024.

Jain; et al.: Review of Unstructured Data Analysis and Parsing Methods. International Conference on Emerging Smart Computing and Informatics (ESCI) pp. 164-169 (2020), XP033812439, DOI: 10.1109/ESCI48226.2020.9167588.

PCT/US2021/050640 International Search Report and Written Opinion dated Dec. 23, 2021.

* cited by examiner

DYNAMIC IN-TRANSIT STRUCTURING OF UNSTRUCTURED MEDICAL DOCUMENTS

CROSS-REFERENCE

This application is a continuation of International Application No. PCT/US2021/050640, filed Sep. 16, 2021, which claims the benefit of U.S. Provisional Patent Application No. 63/080,591, filed Sep. 18, 2020, each of which is incorporated by reference herein in its entirety.

BACKGROUND

In the United States, and in some other countries, medical care may be delivered through a large number of parties: primary care providers, hospitals, insurers, specialty providers, pharmacies, etc. All of these parties may have a need to communicate with each other. For historical reasons, the evolution of the various electronic systems used by these parties may have occurred in a haphazard way, leading to non-interoperable systems as well as a mix of paper and electronic systems.

SUMMARY

The need to protect patient privacy, arising from the Health Insurance Portability and Accountability Act (HIPAA) Act, may discourage the use of email as a method of moving medical information between parties. As a result, the use of facsimile (fax) machines, over plain old telephone service (POTS lines) may be a common or standard method of moving information between parties.

For example, Party A (e.g., a hospital or doctor's office) may deliver to Party B (e.g., an insurance company), via fax, a large unstructured document (e.g. a portable document file or PDF file), in response to a request for information. In the medical domain, the request may be regarding the need for information concerning a medical procedure, for example, to determine eligibility for a claim reimbursement. Because Party A may not know exactly which piece of information Party B requires, Party A may fax significantly more information than is required. Party A may send to Party B all documents relevant to the potential claim, in the form of one large document package. This large document may, for example, comprise several concatenated documents: several MRI interpretation reports, a pathology report, a genomics report, and several clinic notes. The single large document may be hundreds of pages long. Being scanned pages, it may not be indexed at all, and may not be searchable. This method may reduce the number of round trips between Party A and Party B to approve this particular procedure; by having sent 200 pages of unstructured data, Party A may ensure that Party B has the right data element somewhere in the large document. So, although a human being at Party B has to sift and look through the document, the elapsed time may be shorter, because the wait times for several round trips of faxes is eliminated.

Paradoxically, this behavior may slow down the entire medical system, because every party in every transaction may behave the same way. This may clutter the entire system with orders of magnitude more pages of documents being sent via fax, with more humans required to look through more pages to find the useful data elements.

Hundreds of millions to billions of such documents may be routinely faxed between healthcare institutions per year. The process may be inefficient, leading to countless hours of lost time and productivity.

In light of these challenges, recognized herein is a need for more efficient systems and methods for information delivery and intake which can address at least the above-mentioned problems.

The present disclosure provides systems and methods for dynamically transforming an unstructured document to a structured document prior to, during, or subsequent to, transfer of information via the unstructured document. The transformation may be based at least in part on processing a variety of factors, such as the content of the unstructured document, a request from a first party transferring the document, identity or characteristics of the first party, a request from a second party requesting the document, identity or characteristics of the second party, or a combination thereof. Such processing may be performed on demand or in real-time. Such processing may be automated.

In an aspect, provided is a method of creating a structured document package from an unstructured document being transmitted from a first party to a second party, comprising: (a) parsing the unstructured document to create a classification label for each of a plurality of individual subdocuments within the unstructured document; (b) for each subdocument: (i) extracting metadata information per the needs of the first party and the second party, determined based on attributes of the first party and the second party; (ii) transforming the metadata information and classification labels based on the attributes of the second party, and; (iii) packaging the metadata information, classification labels, and a table of contents into a manifest; and (c) packaging the manifest and the plurality of individual subdocuments into the structured document package.

In some embodiments, (c) further comprises packaging the unstructured document into the structured document package.

In another aspect, the present disclosure provides a method for preparing a structured document from an unstructured document for transmission from a first party to a second party, wherein the unstructured document comprises a plurality of sub-documents, the method comprising: (a) parsing the unstructured document to determine a classification label for each of the plurality of sub-documents; (b) for each individual sub-document of the plurality of sub-documents: (i) extracting metadata information from the individual sub-document based at least in part on at least one of an attribute of the first party and an attribute of the second party; and (ii) packaging at least the metadata information and the classification label for the individual sub-document into a manifest; and (c) packaging at least the manifest and the plurality of sub-documents into the structured document package.

In some embodiments, the method further comprises, prior to (a), obtaining the unstructured document from a remote server. In some embodiments, (a) further comprises segmenting the unstructured document into the plurality of sub-documents. In some embodiments, the segmenting comprises determining starting and ending portions of the plurality of sub-documents. In some embodiments, (a) further comprises parsing the unstructured document using one or more algorithms selected from the group consisting of a text recognition algorithm, a regular expressions algorithm, a pattern recognition algorithm, an imaging recognition algorithm, a natural language processing algorithm, an optical character recognition algorithm, a term frequency-inverse document frequency (TF-IDF) algorithm, and a bag-of-words algorithm.

In some embodiments, determining the classification label for each of the plurality of sub-documents comprises determining whether each of the plurality of sub-documents is an imaging report, a pathology report, a clinic note, a progress note, a genomics report, a laboratory test report, a diagnostic report, or a prognostic report. In some embodiments, determining the classification label for each of the plurality of sub-documents comprises using at least one feature selected from the group consisting of content of the unstructured document, report title, fax number, email address, a request from the first party, identity or characteristics of the first party, a request from the second party, and identity or characteristics of the second party. In some embodiments, determining the classification label for each of the plurality of sub-documents comprises processing the at least one feature using a trained machine learning classifier. In some embodiments, the trained machine learning classifier comprises an algorithm selected from the group consisting of a support vector machine, neural network, deep neural network, random forest, and XGBoost.

In some embodiments, the metadata information comprises keywords and/or structure of the individual sub-document. In some embodiments, the metadata information comprises a procedure date, subject information, or treating physician information. In some embodiments, the metadata information comprises a report type of the individual sub-document or a disease type of a subject. In some embodiments, the metadata information comprises information specific to the disease type that is extracted at least in part using ontologies specific to the disease type.

In some embodiments, (b) further comprises transforming the metadata information and the classification label for the individual sub-document based at least in part on the attribute of the second party. In some embodiments, (b) further comprises storing the extracted metadata information in a metadata store prior to the packaging. In some embodiments, (b) further comprises packaging a table of contents into the manifest.

In some embodiments, the method further comprises indexing the plurality of individual sub-documents based at least in part on the metadata information, and the manifest comprises the metadata information in an indexed format. In some embodiments, the indexed format is searchable. In some embodiments, the indexed format comprises a comma separated values (CSV) format or a SQLite database format. In some embodiments, the structured document package comprises a file format selected from the group consisting of a text file, a PDF file, a zip file, or a gzip file. In some embodiments, the structured document package comprises a file format determined at least in part by the attribute of the second party. In some embodiments, the method further comprises encoding the metadata information using ISO/TS 21526:2019, B-trees, hash tables, or document embedding. In some embodiments, (c) further comprises packaging at least the unstructured document into the structured document package.

In some embodiments, the method further comprises transmitting the structured document from the first party to the second party. In some embodiments, the method further comprises transmitting the structured document from the first party to an intermediary, and transmitting the structured document from the intermediary to the second party. In some embodiments, the method further comprises transmitting the structured document to a remote server that is accessible by the second party. In some embodiments, the transmitting comprises use of electronic mail. In some embodiments, the transmitting comprises use of facsimile transmission.

In some embodiments, the unstructured document comprises a portable document file (PDF).

In another aspect, the present disclosure provides a system for preparing a structured document from an unstructured document for transmission from a first party to a second party, comprising: a database that is configured to store the unstructured document, wherein the unstructured document comprises a plurality of sub-documents; and one or more computer processors operatively coupled to the database, wherein the one or more computer processors are individually or collectively programmed to: (a) parse the unstructured document to determine a classification label for each of the plurality of sub-documents; (b) for each individual sub-document of the plurality of sub-documents: (i) extract metadata information from the individual sub-document based at least in part on at least one of an attribute of the first party and an attribute of the second party; and (ii) package at least the metadata information and the classification label for the individual sub-document into a manifest; and (c) package at least the manifest and the plurality of sub-documents into the structured document package.

In some embodiments, the one or more computer processors are individually or collectively programmed to further, prior to (a), obtaining the unstructured document from a remote server. In some embodiments, (a) further comprises segmenting the unstructured document into the plurality of sub-documents. In some embodiments, the segmenting comprises determining starting and ending portions of the plurality of sub-documents. In some embodiments, (a) further comprises parsing the unstructured document using one or more algorithms selected from the group consisting of a text recognition algorithm, a regular expressions algorithm, a pattern recognition algorithm, an imaging recognition algorithm, a natural language processing algorithm, an optical character recognition algorithm, a term frequency-inverse document frequency (TF-IDF) algorithm, and a bag-of-words algorithm.

In some embodiments, determining the classification label for each of the plurality of sub-documents comprises determining whether each of the plurality of sub-documents is an imaging report, a pathology report, a clinic note, a progress note, a genomics report, a laboratory test report, a diagnostic report, or a prognostic report. In some embodiments, determining the classification label for each of the plurality of sub-documents comprises using at least one feature selected from the group consisting of content of the unstructured document, report title, fax number, email address, a request from the first party, identity or characteristics of the first party, a request from the second party, and identity or characteristics of the second party. In some embodiments, determining the classification label for each of the plurality of sub-documents comprises processing the at least one feature using a trained machine learning classifier. In some embodiments, the trained machine learning classifier comprises an algorithm selected from the group consisting of a support vector machine, neural network, deep neural network, random forest, and XGBoost.

In some embodiments, the metadata information comprises keywords and/or structure of the individual sub-document. In some embodiments, the metadata information comprises a procedure date, subject information, or treating physician information. In some embodiments, the metadata information comprises a report type of the individual sub-document or a disease type of a subject. In some embodiments, the metadata information comprises information specific to the disease type that is extracted at least in part using ontologies specific to the disease type.

In some embodiments, (b) further comprises transforming the metadata information and the classification label for the individual sub-document based at least in part on the attribute of the second party. In some embodiments, (b) further comprises storing the extracted metadata information in a metadata store prior to the packaging. In some embodiments, (b) further comprises packaging a table of contents into the manifest.

In some embodiments, the one or more computer processors are individually or collectively programmed to further index the plurality of individual sub-documents based at least in part on the metadata information, and the manifest comprises the metadata information in an indexed format. In some embodiments, the indexed format is searchable. In some embodiments, the indexed format comprises a comma separated values (CSV) format or a SQLite database format. In some embodiments, the structured document package comprises a file format selected from the group consisting of a text file, a PDF file, a zip file, or a gzip file. In some embodiments, the structured document package comprises a file format determined at least in part by the attribute of the second party. In some embodiments, the one or more computer processors are individually or collectively programmed to further encode the metadata information using ISO/TS 21526:2019, B-trees, hash tables, or document embedding. In some embodiments, (c) further comprises packaging at least the unstructured document into the structured document package.

In some embodiments, the one or more computer processors are individually or collectively programmed to further transmit the structured document from the first party to the second party. In some embodiments, the one or more computer processors are individually or collectively programmed to further transmit the structured document from the first party to an intermediary, and transmit the structured document from the intermediary to the second party. In some embodiments, the one or more computer processors are individually or collectively programmed to further transmit the structured document to a remote server that is accessible by the second party. In some embodiments, the transmitting comprises use of electronic mail. In some embodiments, the transmitting comprises use of facsimile transmission.

In some embodiments, the unstructured document comprises a portable document file (PDF).

In another aspect, the present disclosure provides a non-transitory computer-readable medium comprising machine-executable code that, upon execution by one or more computer processors, implements a method for preparing a structured document from an unstructured document for transmission from a first party to a second party, wherein the unstructured document comprises a plurality of sub-documents, the method comprising: (a) parsing the unstructured document to determine a classification label for each of the plurality of sub-documents; (b) for each individual sub-document of the plurality of sub-documents: (i) extracting metadata information from the individual sub-document based at least in part on at least one of an attribute of the first party and an attribute of the second party; and (ii) packaging at least the metadata information and the classification label for the individual sub-document into a manifest; and (c) packaging at least the manifest and the plurality of sub-documents into the structured document package.

In some embodiments, the method further comprises, prior to (a), obtaining the unstructured document from a remote server. In some embodiments, (a) further comprises segmenting the unstructured document into the plurality of sub-documents. In some embodiments, the segmenting comprises determining starting and ending portions of the plurality of sub-documents. In some embodiments, (a) further comprises parsing the unstructured document using one or more algorithms selected from the group consisting of a text recognition algorithm, a regular expressions algorithm, a pattern recognition algorithm, an imaging recognition algorithm, a natural language processing algorithm, an optical character recognition algorithm, a term frequency-inverse document frequency (TF-IDF) algorithm, and a bag-of-words algorithm.

In some embodiments, determining the classification label for each of the plurality of sub-documents comprises determining whether each of the plurality of sub-documents is an imaging report, a pathology report, a clinic note, a progress note, a genomics report, a laboratory test report, a diagnostic report, or a prognostic report. In some embodiments, determining the classification label for each of the plurality of sub-documents comprises using at least one feature selected from the group consisting of content of the unstructured document, report title, fax number, email address, a request from the first party, identity or characteristics of the first party, a request from the second party, and identity or characteristics of the second party. In some embodiments, determining the classification label for each of the plurality of sub-documents comprises processing the at least one feature using a trained machine learning classifier. In some embodiments, the trained machine learning classifier comprises an algorithm selected from the group consisting of a support vector machine, neural network, deep neural network, random forest, and XGBoost.

In some embodiments, the metadata information comprises keywords and/or structure of the individual sub-document. In some embodiments, the metadata information comprises a procedure date, subject information, or treating physician information. In some embodiments, the metadata information comprises a report type of the individual sub-document or a disease type of a subject. In some embodiments, the metadata information comprises information specific to the disease type that is extracted at least in part using ontologies specific to the disease type.

In some embodiments, (b) further comprises transforming the metadata information and the classification label for the individual sub-document based at least in part on the attribute of the second party. In some embodiments, (b) further comprises storing the extracted metadata information in a metadata store prior to the packaging. In some embodiments, (b) further comprises packaging a table of contents into the manifest.

In some embodiments, the method further comprises indexing the plurality of individual sub-documents based at least in part on the metadata information, and the manifest comprises the metadata information in an indexed format. In some embodiments, the indexed format is searchable. In some embodiments, the indexed format comprises a comma separated values (CSV) format or a SQLite database format. In some embodiments, the structured document package comprises a file format selected from the group consisting of a text file, a PDF file, a zip file, or a gzip file. In some embodiments, the structured document package comprises a file format determined at least in part by the attribute of the second party. In some embodiments, the method further comprises encoding the metadata information using ISO/TS 21526:2019, B-trees, hash tables, or document embedding. In some embodiments, (c) further comprises packaging at least the unstructured document into the structured document package.

In some embodiments, the method further comprises transmitting the structured document from the first party to the second party. In some embodiments, the method further comprises transmitting the structured document from the first party to an intermediary, and transmitting the structured document from the intermediary to the second party. In some embodiments, the method further comprises transmitting the structured document to a remote server that is accessible by the second party. In some embodiments, the transmitting comprises use of electronic mail. In some embodiments, the transmitting comprises use of facsimile transmission.

In some embodiments, the unstructured document comprises a portable document file (PDF).

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein) of which:

DETAILED DESCRIPTION

Figure 1:
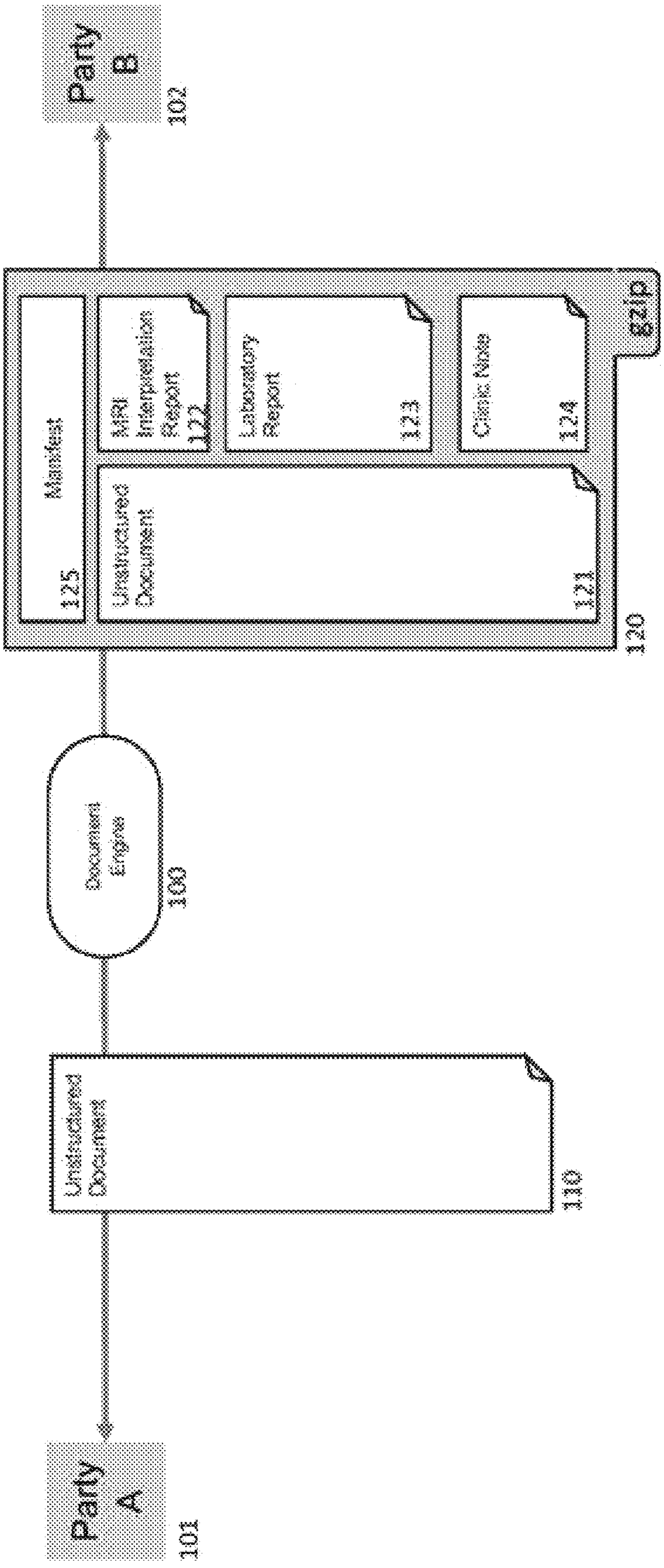
FIG. 1 illustrates an example of a Document Engine configured to transform an unstructured document to a structured document package.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Provided herein are methods and systems for transforming an unstructured document, which is delivered from a first party (e.g., a sending party) to a second party (e.g., a receiving party) needing to receive information (e.g., medical information), to a structured form. The structured form may be tailored to the needs of the second party and based on the identity and/or characteristics of the second party. Provided herein are methods and systems for packaging this transformed structure so that it may be transmitted over a computer network or other media.

This systems and methods may implement a Document Engine, which may be located on the premises of a sending party, a receiving party, or a services provider, such as an intermediary party with access to a document in transit between the sending party and the receiving party. The Document Engine may be located at, and/or be accessible from, one or more remote servers. The Document Engine may be located at, and/or be accessible from, one or more local servers, such as at the sending party, receiving party, and/or services provider site. The Document Engine may read the pages (or other components) of unstructured documents, parsing and understanding them well enough to determine the start and end of the individual reports contained therein. For example, the Document Engine may implement any text, pattern, and/or imaging recognition algorithms, or any combination thereof, to read the information relayed in the unstructured documents. The Document Engine may implement natural language processing algorithms.

After doing so, the Document Engine may split the original unstructured document into constituent subdocuments. Then, the Document Engine may further analyze each of the constituent subdocuments to determine the classification of the document. For example, the Document Engine may determine whether the document is an imaging report, pathology report, clinic note, genomics report, etc.

After the classification, the Document Engine may further extract salient keywords and structure (e.g., as metadata) from the subdocuments. Some of this metadata may be generic, such as dates of procedures, name of subject (e.g., patient), names of treating physicians, etc. Some of this metadata may be domain specific—that is, specific to the type of report, and to the type of disease the subject or patient has. For example, if one report type is "Patient Summary" which states that the subject's disease condition is "Midline Glioma," a cancer-specific ontology may be used to extract cancer-specific terms for other reports.

Any information contained within, or provided in addition to, the unstructured document may be used during classification of the document, or subdocuments thereof, such as the content of the unstructured document, a request from a first party transferring the document, identity or characteristics of the first party, a request from a second party requesting the document, identity or characteristics of the second party, or a combination thereof.

After the subdocuments are classified, metadata may be extracted. Then, the Document Engine may assemble a structured document package that comprises the original unstructured document, the subdocuments, and a manifest. The manifest may comprise a table of contents of the documents in the structured document package, in addition to the indexed metadata which has been extracted. With this, the recipient of the structured document package may easily find the exact required subdocument—for example, the magnetic resonance imaging (MRI) interpretation report for Jul. 12, 2016, or the most recent genomics report that references an epidermal growth factor receptor (EGFR) mutation—without having to search through an entirety of an unstructured document that is hundreds of pages or even thousands of pages long.

FIG. 1 depicts a high-level overview of the workings of a system of the present disclosure, embodied in Document Engine 100, in the context of the movement and translation of an unstructured document 110 from Party A 101 to a structured document package 120 delivered to Party B 102.

The system of the present disclosure may comprise a Document Engine 100, which may take as input a single scanned unstructured document 110 (such as a scanned PDF document), which may contain a multitude of reports concatenated together, which it may receive from Party A 101.

The Document Engine may receive the unstructured document from Party A via any mechanism. For example, the transport may be via email or fax. The transport may be via direct scanning. The Document Engine may receive any digital format of a document. Though examples of the present disclosure describe manipulation of an initially "unstructured" document, the same systems and methods may transform a first form of structured document (e.g., indexed and/or packaged in a first format) to a second form of structured document (e.g., indexed and/or packaged in a second format). In some examples, a first form of structured document may be first flattened into an unstructured document, for further processing into the second format.

The Document Engine may read the pages of this document, parsing and understanding them well enough to determine the start and end of the individual reports contained therein. It may split the original document into constituent subdocuments, in this case determining that there are three subdocuments 122, 123, and 124. Subdocument classification may be performed, and subdocument metadata may be extracted, by methods described herein.

The Document Engine 100 may create a structured document package 120 comprising the individual classified subdocuments 122, 123, and 124, and a manifest 125. The manifest may comprise a table of contents that identifies each of the labeled, classified subdocuments, as well as indexes of the keywords extracted from the subdocuments. In some instances, the Document Engine also comprises a copy of the original unstructured document 121 in the package. Alternatively, the copy may be omitted. The Document Engine may compress the structured document package, using a compression algorithm such as gzip or zip.

The structured document package may then be transferred from the Document Engine 100 to recipient Party B 102. As with the transfer from Part A to the Document Engine, any transfer method may be used.

Party B may access the appropriate documents by consulting the manifest, and then accessing the appropriate document(s) as pointed to by the manifest, rather than needing to serially search the entire original file. Advantageously, this can save significant amounts of time.

The Document Engine may be provided information on the recipient party's capabilities and/or identity, and therefore may tailor the structured document package according to the needs of the recipient's computer systems. For example, depending on the recipient's capabilities, the structured document package may be a PDF file, and the manifest may be structured as annotated thumbnails in a PDF viewer. For example, depending on the recipient's capabilities, the structured document package and the manifest may be structured as PDF chapter headings and subparagraphs inserted into the unstructured document. For example, depending on the recipient's capabilities, the structured document package may be a zip file, and the manifest may be structured as a directory structure with zero or more additional files in a zip archive.

Figure 2:
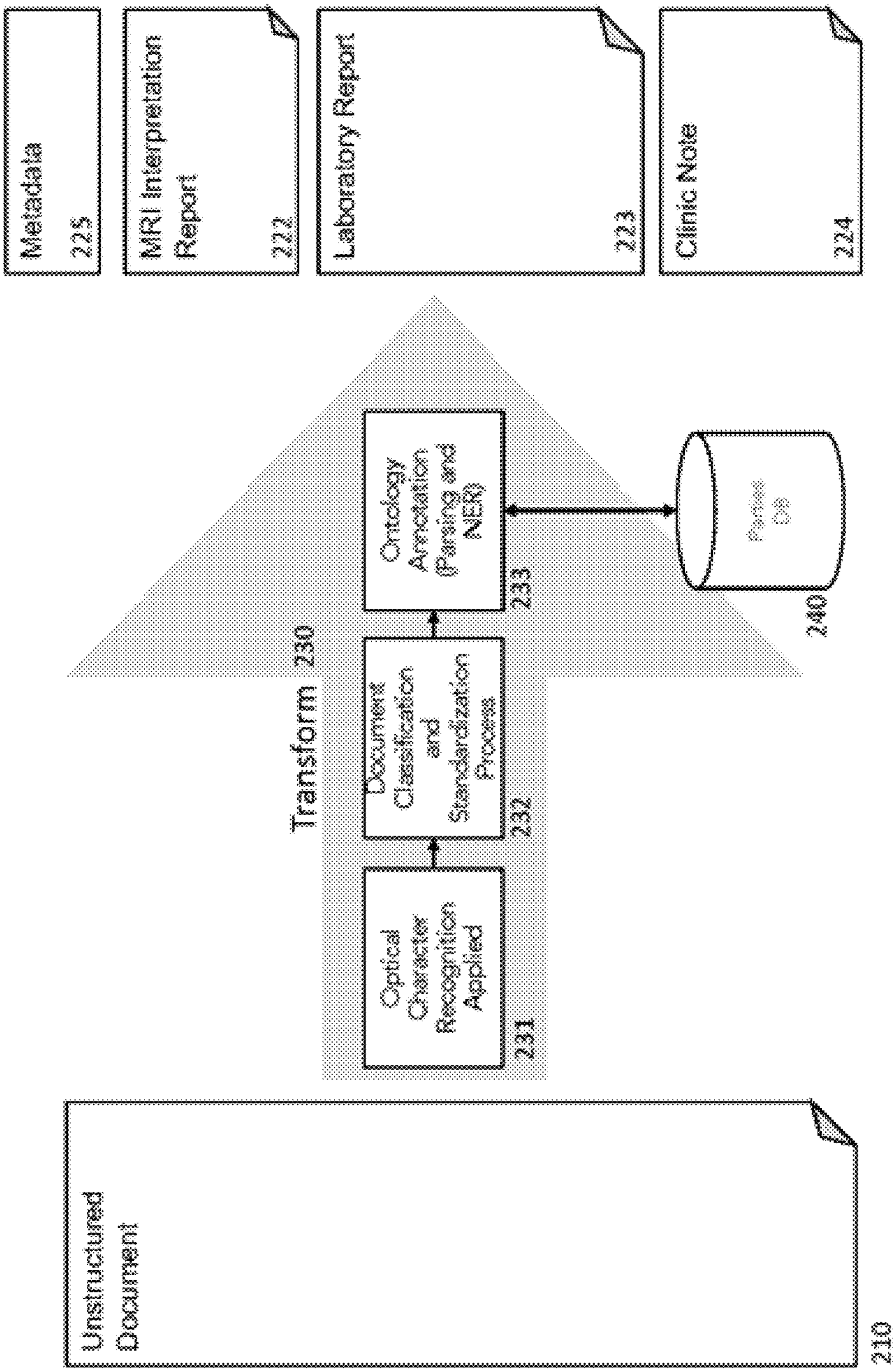
FIG. 2 illustrates an example of a schematic overview of parsing and parceling of an unstructured document into distinct subdocuments.

FIG. 2 depicts the operations performed in the initial parsing and parceling of the unstructured document into distinct subdocuments. The initial unstructured document 210 may be fed through Transform system 230 to generate subdocuments. In general, an arbitrary number of subdocuments may be found. In this example, three subdocuments are found: subdocuments 222, 223, and 224. The Transform process may be broken down into several operations. First, the document may be fed through optical character recognition software 231, and then into a classifier system 232. In some embodiments, a support vector machine, neural network, deep neural network, random forest, XGBoost, or other algorithms may be used in the classifier system. This may be in conjunction with other algorithms such as term frequency-inverse document frequency (TF-IDF) or bag-of-words. The specific choice of algorithms may depend on the exact domain, with acute disease and precision oncology potentially behaving differently than, for example, chronic disease.

Oncology parsing and named entity extraction 233 may require deep knowledge about the specific domain, such as oncology. It may also require significant knowledge such as generic medicines, common misspellings, the routes by which medications are administered, etc. Some of this knowledge may be specific to the parties between which the documents are being transferred. For example, what sending Party A calls a "Clinic Note," receiving Party B may call a "Progress Note." These translations may be accommodated automatically by consulting translation tables in parties database 240.

As metadata is accumulated, it may be stored in metadata store 225, until it is ready to be packaged later.

Figure 3:
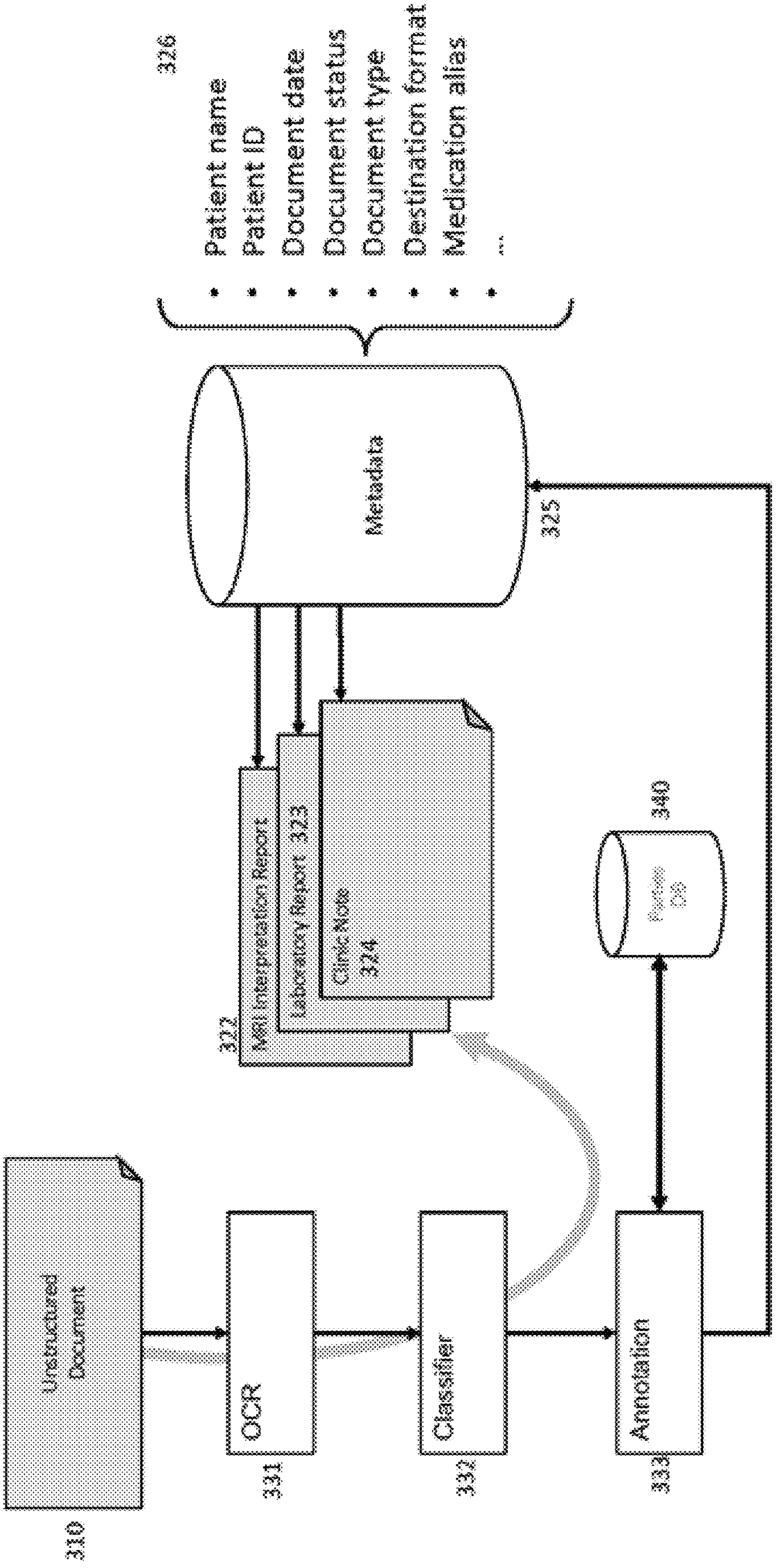
FIG. 3 illustrates an example of a schematic flowchart of document transformation operations.

FIG. 3 outlines the flowchart of the transform operations in more detail. As the unstructured document 310 is analyzed, it first may be processed by optical character recognition 331, and then the classifier 332 may separate it into distinct subdocuments 322, 323, and 324. The annotation module may work in concert with the parties database 340, to add metadata to each of the subdocuments, which is stored in the metadata store 325. This is depicted here as a database, but may be implemented as a file, an in-memory database, or as a traditional database. Its contents, once complete, may be combined with a table of contents to form the manifest file. Example metadata items are shown in list 326. Note that some metadata items, such as "Destination format," may not be a function of the document itself, but rather of the document plus attributes of the eventual recipient.

Figure 4:
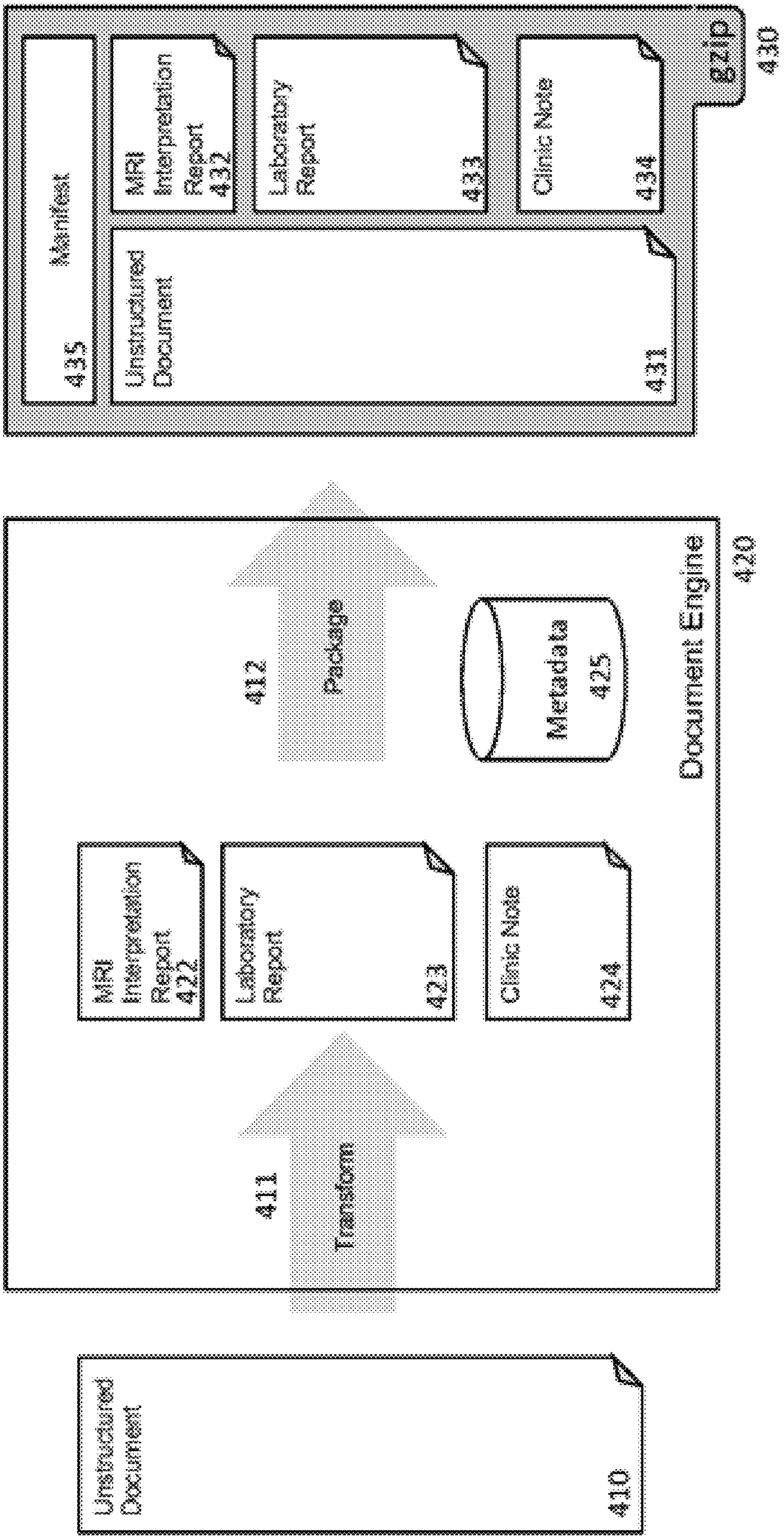
FIG. 4 illustrates an example of a schematic overview of packaging of constituent subdocuments and metadata to a structured document package.

FIG. 4 illustrates how the constituent subdocuments and metadata are packaged for shipment to the recipient. This packaging may depend on the capabilities the recipient has for handling metadata. In this example, an assumption is that the recipient has minimal capability but may like to potentially do some complex queries on the metadata, so the final data may be packaged as a gzip file with a directory structure that contains the metadata both as a comma separated values (CSV) file and as a SQLite database file.

The initial unstructured document 410 may be decomposed into constituent subdocuments 422, 423, and 424 via the Transform process 411, and may reside, along with the metadata in temporary metadata database 425, in the Document Engine 420. The Document Engine may have previously, via parties database 340 of FIG. 3, determined that the recipient prefers a gzip file that includes a SQLite version of the metadata.

Therefore, for package operation 412, the Document Engine may extract the metadata from metadata database 425 in both CSV and SQLite forms, and may pipe those to the metadata directory of the target directory that is to be gzipped. It may also add the files for subdocuments 422, 423, and 424, as well as a copy of the original unstructured document 410. At this point the directory to be gzipped may look like:

```
./manifest/manifest.csv
./manifest/manifest.db
./in/Unstructured_Document.pdf
./out/MRI_Interpretation_Report.pdf
./out/Laboratory_Report.pdf
./out/Clinic_Note.pdf
```

This directory may be then gzipped into one file 430 and may be ready for transmission to the recipient. It may comprise Unstructured Document 431, MRI Interpretation Report 432, Laboratory Report 433, and Clinic Note 434. The manifest 435 may be a directory consisting of two files in this instance.

This example is for illustrative purposes only, and is not intended to limit the scope of the present disclosure. For example, the metadata may be encoded using standards such as ISO/TS 21526:2019. Alternatively, it may be encoded using B-trees, hash tables, or other mechanisms. It may be directly embedded in PDF documents using Adobe's editing tools, e.g., if the amount of metadata is small enough.

Figure 5:
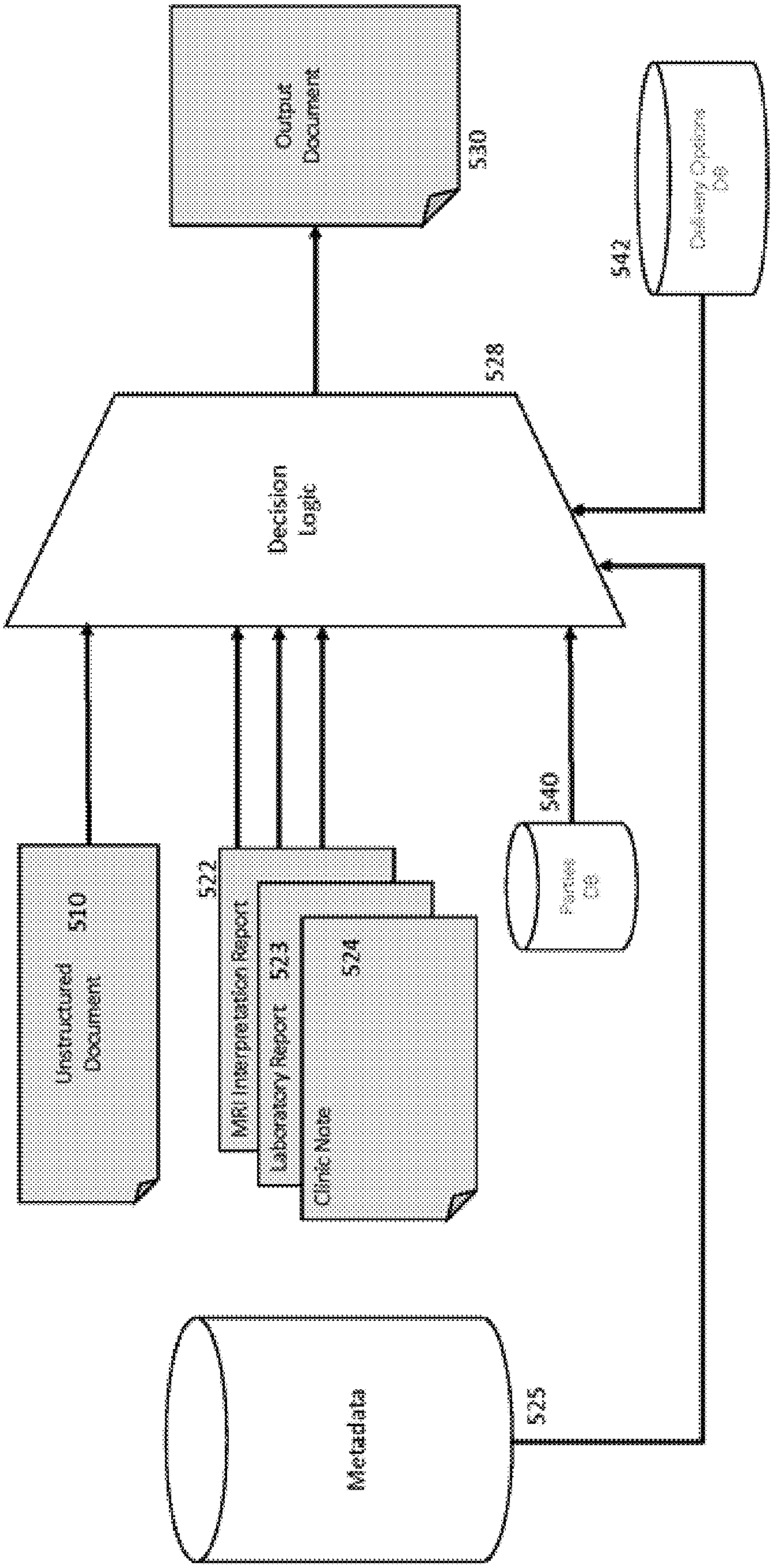
FIG. 5 illustrates an example of a schematic data flow to creating an output package for transmittal to a receiving party.

FIG. 5 shows the data flow to create the single output document that is sent to the receiving party. The original unstructured document 510, plus any subdocuments that were extracted in the Transform process 411 of FIG. 4 (in this example, the three subdocuments 522, 523, and 524), may flow into Decision Logic 528, where they may be combined to create the Output Document 530. The exact form of that document (whether it is a PDF file, a zip file, gzip file, etc.) may depend on the recipient's preferences, as stored in the parties database 540.

Based on the lookup in the parties database, the Decision Logic may use a set of defaults and configuration options stored in delivery options database 542 to decide how to package the Output Document 530. For example, a default rule may state:

"If there is no data about the recipient in the parties database, then use a zip file for delivery, with the manifest data stored in a CSV file"

Other rules may govern specific institutions, or types of institutions (e.g., Medicare facilities). Through the combination of the delivery options database and the parties database data, it may be guaranteed that the Decision Logic may have a path forward for creating an Output Document.

Note that while the Document Engine may be agnostic as to mode of delivery of the document (email, fax, carrier pigeon, etc.), the systems and methods may become more efficient when aware of the functional attributes of where documents are to be sent (Can the recipient read zip files? Can they read PDFs with rich markup?), or sometimes, where they originate. Therefore, the Document Engine may comprise or provide a directory service or mail service, where headers may provide the identity of the sender and the intended recipient.

While systems and methods of the present disclosure have been described in the context of its input and/or output behavior, the actual apparatus implementing the Document Engine may be placed in a physical location. Consideration of this location may affect how the operator of a Document Engine considers the use of directory services.

Figure 6A:
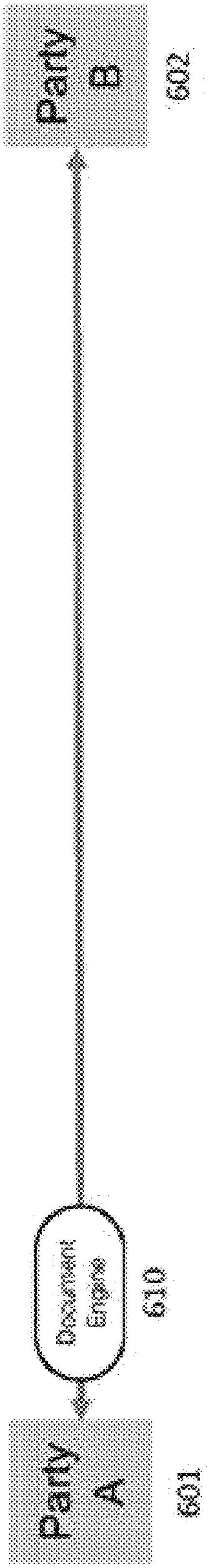
FIG. 6A and FIG. 6B schematically illustrate examples of placements of a Document Engine.

FIG. 6A shows the placement of a Document Engine co-resident with the sender of unstructured documents. In this location, Party A 601 may utilize a Document Engine 610 to send documents to any number of third parties. One such third party may be shown as Party B 602. Party A may wish that all third parties receive structured documents. Party A may therefore maintain a registry of the attributes of the receiving parties, in order to tailor the output documents to their needs. Thus, the systems and methods of the present may use a registry for such a directory service.

Figure 6B:
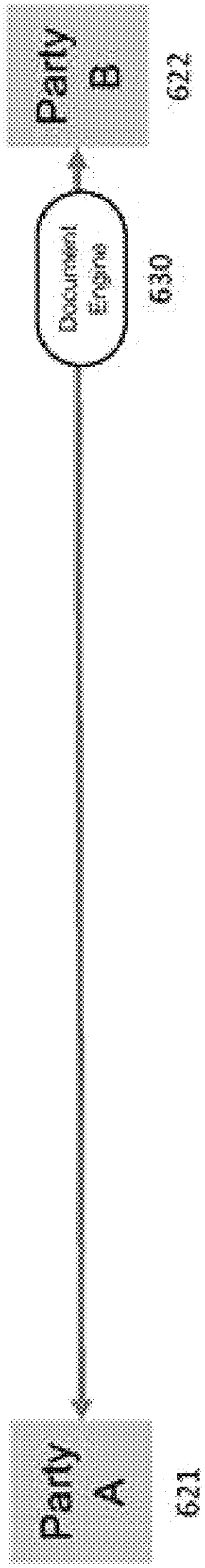

FIG. 6B shows the placement of a Document Engine co-resident with the receiver of unstructured documents. In this location, Party B 622 may utilize a Document Engine 630 to receive documents from any number of third parties. One such third party may be Party A 621. Party B may have knowledge of what capabilities it has to read formats and understand metadata; however, it may be a very large burden to ensure that it is able to parse the largest possible number of input formats possible, therefore this may be an expensive configuration to maintain.

Figure 7:
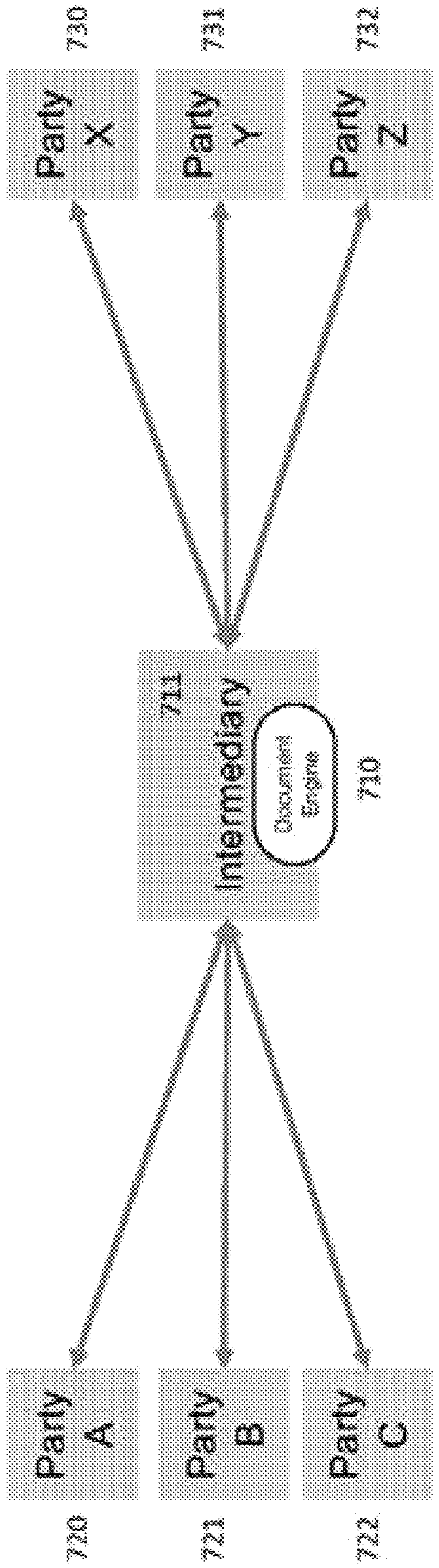
FIG. 7 schematically illustrates an example of an intermediary implementing a Document Engine.

FIG. 7 depicts a Document Engine 710 which may be run by an Intermediary 711, a provider of document structuring as a service. The Intermediary may receive unstructured documents from an arbitrary number of sources (in this example, three are shown: Party A 720, Party B 721, and Party C 722), structure the documents, and send the structured document packages on to arbitrary receivers (in this example, three are shown: Party X 730, Party Y 731, and Party Z 732). In some embodiments, a party who is a sender in one transaction may be a receiver in another transaction.

The Intermediary may have an advantage of being able to build a directory service that is more robust more quickly, and to amortize the costs of accommodating different formats across a larger group of participants, making this configuration more economical.

Computer Systems

Figure 8:
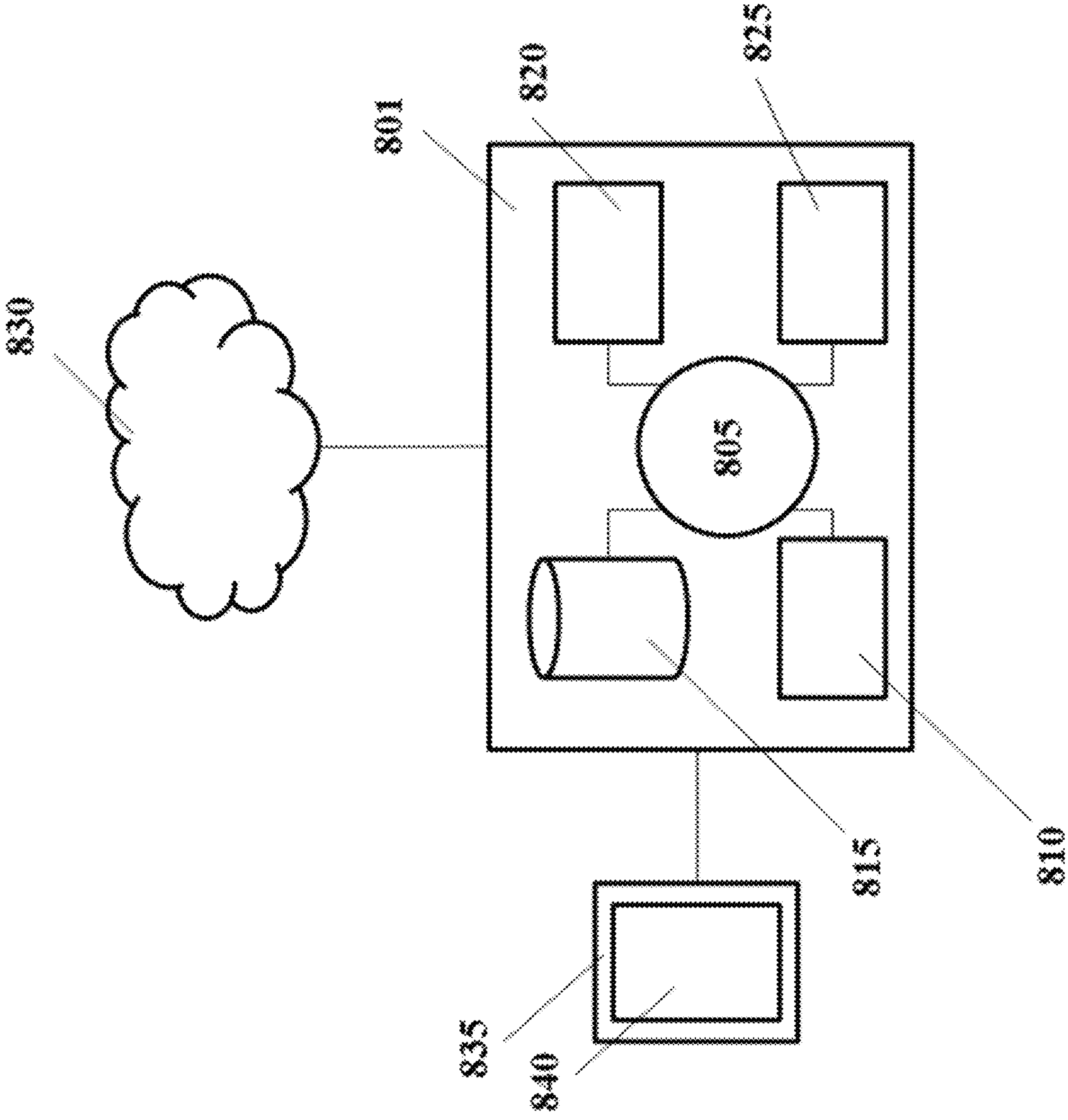
FIG. 8 illustrates an example of a computer system programmed to implement methods and systems of the present disclosure.

The present disclosure provides computer systems that are programmed to implement methods of the disclosure. FIG. 8 shows a computer system 801 that is programmed or otherwise configured to implement systems and methods of the present disclosure. The computer system 801 can implement and regulate various aspects of, for example, the Document Engine, of the present disclosure. The computer system 801 can be an electronic device of a user or a computer system that is remotely located with respect to the electronic device. The electronic device can be a mobile electronic device. For example, the computer system can be an electronic device of a sender or recipient, or a computer system that is remotely located with respect to the sender or recipient.

The computer system 801 includes a central processing unit (CPU, also "processor" and "computer processor" herein) 805, which can be a single core or multi core processor, or a plurality of processors for parallel processing. The computer system 801 also includes memory or memory location 810 (e.g., random-access memory, read-only memory, flash memory), electronic storage unit 815 (e.g., hard disk), communication interface 820 (e.g., network adapter) for communicating with one or more other systems, and peripheral devices 825, such as cache, other memory, data storage and/or electronic display adapters. The memory 810, storage unit 815, interface 820 and peripheral devices 825 are in communication with the CPU 805 through a communication bus (solid lines), such as a motherboard. The storage unit 815 can be a data storage unit (or data repository) for storing data. The computer system 801 can be operatively coupled to a computer network ("network") 830 with the aid of the communication interface 820. The network 830 can be the Internet, an internet and/or extranet, or an intranet and/or extranet that is in communication with the Internet. The network 830 in some cases is a telecommunication and/or data network. The network 830 can include one or more computer servers, which can enable distributed computing, such as cloud computing. The network 830, in some cases with the aid of the computer system 801, can implement a peer-to-peer network, which may enable devices coupled to the computer system 801 to behave as a client or a server.

The CPU 805 can execute a sequence of machine-readable instructions, which can be embodied in a program or software. The instructions may be stored in a memory location, such as the memory 810. The instructions can be directed to the CPU 805, which can subsequently program or otherwise configure the CPU 805 to implement methods of the present disclosure. Examples of operations performed by the CPU 805 can include fetch, decode, execute, and writeback.

The CPU 805 can be part of a circuit, such as an integrated circuit. One or more other components of the system 801 can be included in the circuit. In some cases, the circuit is an application specific integrated circuit (ASIC).

The storage unit 815 can store files, such as drivers, libraries and saved programs. The storage unit 815 can store user data, e.g., user preferences and user programs. The computer system 801 in some cases can include one or more additional data storage units that are external to the computer system 801, such as located on a remote server that is in communication with the computer system 801 through an intranet or the Internet.

The computer system 801 can communicate with one or more remote computer systems through the network 830. For instance, the computer system 801 can communicate with a remote computer system of a user (e.g., sender, recipient, etc.). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 801 via the network 830.

Methods as described herein can be implemented by way of machine (e.g., computer processor) executable code stored on an electronic storage location of the computer system 801, such as, for example, on the memory 810 or electronic storage unit 815. The machine executable or machine readable code can be provided in the form of software. During use, the code can be executed by the processor 805. In some cases, the code can be retrieved from the storage unit 815 and stored on the memory 810 for ready access by the processor 805. In some situations, the electronic storage unit 815 can be precluded, and machine-executable instructions are stored on memory 810.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 801, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 801 can include or be in communication with an electronic display 835 that comprises a user interface (UI) 840 for providing, for example, an instructions panel of document restructuring, input/output preview, etc. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 805.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for preparing a structured document from an unstructured document for transmission from a first party to a second party, wherein the unstructured document comprises a plurality of sub-documents, the method comprising:

(a) parsing the unstructured document to determine a classification label for each of the plurality of sub-documents;

(b) for each individual sub-document of the plurality of sub-documents:

(i) extracting metadata information from the individual sub-document based at least in part on at least one of an attribute of the first party and an attribute of the second party, wherein the metadata information comprises a report type of the individual sub-document or a disease type of a subject, and wherein the metadata information comprises information specific to the disease type that is extracted at least in part using ontologies specific to the disease type; and (ii) packaging at least the metadata information and the classification label for the individual sub-document into a manifest;

(c) packaging at least the manifest and the plurality of sub-documents into the structured document package; and (d) transmitting the structured document from the first party to the second party.

2. The method of claim 1, further comprising, prior to (a), obtaining the unstructured document from a remote server.

3. The method of claim 1, wherein (a) further comprises segmenting the unstructured document into the plurality of sub-documents.

4. The method of claim 3, wherein the segmenting further comprises determining starting and ending portions of the plurality of sub-documents.

5. The method of claim 1, wherein (a) further comprises parsing the unstructured document using one or more algorithms selected from the group consisting of a text recognition algorithm, a regular expressions algorithm, a pattern recognition algorithm, an imaging recognition algorithm, a natural language processing algorithm, an optical character recognition algorithm, a term frequency-inverse document frequency (TF-IDF) algorithm, and a bag-of-words algorithm.

6. The method of claim 1, wherein determining the classification label for each of the plurality of sub-documents further comprises determining whether each of the plurality of sub-documents is an imaging report, a pathology report, a clinic note, a progress note, a genomics report, a laboratory test report, a diagnostic report, or a prognostic report.

7. The method of claim 1, wherein determining the classification label for each of the plurality of sub-documents further comprises using at least one feature selected from the group consisting of content of the unstructured document, report title, fax number, email address, a request from the first party, identity or characteristics of the first party, a request from the second party, and identity or characteristics of the second party.

8. The method of claim 7, wherein determining the classification label for each of the plurality of sub-documents further comprises processing the at least one feature using a trained machine learning classifier.

9. The method of claim 8, wherein the trained machine learning classifier comprises an algorithm selected from the group consisting of a support vector machine, neural network, deep neural network, random forest, and XGBoost.

10. The method of claim 1, wherein the metadata information comprises keywords or structure of the individual sub-document.

11. The method of claim 1, wherein the metadata information comprises a procedure date, subject information, or treating physician information.

12. The method of claim 1, wherein (b) further comprises transforming the metadata information and the classification label for the individual sub-document based at least in part on the attribute of the second party.

13. The method of claim 1, wherein (b) further comprises storing the extracted metadata information in a metadata store prior to packaging at least the metadata information and the classification label.

14. The method of claim 1, wherein (b) further comprises packaging a table of contents into the manifest.

15. The method of claim 1, further comprising indexing the plurality of individual sub-documents based at least in part on the metadata information, and wherein the manifest comprises the metadata information in an indexed format.

16. The method of claim 15, wherein the indexed format is searchable.

17. The method of claim 15, wherein the indexed format comprises a comma separated values (CSV) format or a SQLite database format.

18. The method of claim 1, wherein the structured document comprises a file format selected from the group consisting of a text file, a PDF file, a zip file, and a gzip file.

19. The method of claim 1, wherein the structured document comprises a file format determined at least in part by the attribute of the second party.

20. A method for preparing a structured document from an unstructured document for transmission from a first party to a second party, wherein the unstructured document comprises a plurality of sub-documents, the method comprising:

(a) parsing the unstructured document to determine a classification label for each of the plurality of sub-documents;

(b) for each individual sub-document of the plurality of sub-documents:

(i) extracting metadata information from the individual sub-document based at least in part on at least one of an attribute of the first party and an attribute of the second party, (ii) encoding the metadata information using ISO/TS 21526:2019, B-trees, hash tables, or document embedding; and (iii) packaging at least the metadata information and the classification label for the individual sub-document into a manifest;

(c) packaging at least the manifest and the plurality of sub-documents into the structured document; and (d) transmitting the structured document from the first party to the second party.

21. The method of claim 1, wherein (c) further comprises packaging at least the unstructured document into the structured document.

22. The method of claim 1, wherein (d) further comprises transmitting the structured document from the first party to an intermediary, and transmitting the structured document from the intermediary to the second party.

23. The method of claim 1, wherein (d) further comprises transmitting the structured document to a remote server that is accessible by the second party.

24. The method of claim 1, wherein the transmitting further comprises use of electronic mail.

25. The method of claim 1, wherein the transmitting further comprises use of facsimile transmission.

26. The method of claim 1, wherein the unstructured document comprises a portable document file (PDF).

27. The method of claim 20, further comprising, prior to (a), obtaining the unstructured document from a remote server.

28. The method of claim 20, wherein (a) further comprises segmenting the unstructured document into the plurality of sub-documents.

29. The method of claim 28, wherein the segmenting further comprises determining starting and ending portions of the plurality of sub-documents.

30. The method of claim 20, wherein (a) further comprises parsing the unstructured document using one or more algorithms selected from the group consisting of a text recognition algorithm, a regular expressions algorithm, a pattern recognition algorithm, an imaging recognition algorithm, a natural language processing algorithm, an optical character recognition algorithm, a term frequency-inverse document frequency (TF-IDF) algorithm, and a bag-of-words algorithm.

31. The method of claim 20, wherein determining the classification label for each of the plurality of sub-documents further comprises determining whether each of the plurality of sub-documents is an imaging report, a pathology report, a clinic note, a progress note, a genomics report, a laboratory test report, a diagnostic report, or a prognostic report.

32. The method of claim 20, wherein determining the classification label for each of the plurality of sub-documents further comprises using at least one feature selected from the group consisting of content of the unstructured document, report title, fax number, email address, a request from the first party, identity or characteristics of the first party, a request from the second party, and identity or characteristics of the second party.

33. The method of claim 32, wherein determining the classification label for each of the plurality of sub-documents further comprises processing the at least one feature using a trained machine learning classifier.

34. The method of claim 33, wherein the trained machine learning classifier comprises an algorithm selected from the group consisting of a support vector machine, neural network, deep neural network, random forest, and XGBoost.

35. The method of claim 20, wherein the metadata information comprises keywords or structure of the individual sub-document.

36. The method of claim 20, wherein the metadata information comprises a procedure date, subject information, or treating physician information.

37. The method of claim 20, wherein (b) further comprises transforming the metadata information and the classification label for the individual sub-document based at least in part on the attribute of the second party.

38. The method of claim 20, wherein (b) further comprises storing the extracted metadata information in a metadata store prior to packaging at least the metadata information and the classification label.

39. The method of claim 20, wherein (b) further comprises packaging a table of contents into the manifest.

40. The method of claim 20, further comprising indexing the plurality of individual sub-documents based at least in part on the metadata information, and wherein the manifest comprises the metadata information in an indexed format.

41. The method of claim 40, wherein the indexed format is searchable.

42. The method of claim 40, wherein the indexed format comprises a comma separated values (CSV) format or a SQLite database format.

43. The method of claim 20, wherein the structured document comprises a file format selected from the group consisting of a text file, a PDF file, a zip file, and a gzip file.

44. The method of claim 20, wherein the structured document comprises a file format determined at least in part by the attribute of the second party.

45. The method of claim 20, wherein (c) further comprises packaging at least the unstructured document into the structured document.

46. The method of claim 20, wherein (d) further comprises transmitting the structured document from the first party to an intermediary, and transmitting the structured document from the intermediary to the second party.

47. The method of claim 20, wherein (d) further comprises transmitting the structured document to a remote server that is accessible by the second party.

48. The method of claim 20, wherein the transmitting further comprises use of electronic mail.

49. The method of claim 20, wherein the transmitting further comprises use of facsimile transmission.

50. The method of claim 20, wherein the unstructured document comprises a portable document file (PDF).

* * * * *